United States Patent [19]

Unger

[11] Patent Number: 4,729,843

[45] Date of Patent: Mar. 8, 1988

[54] MIXTURES OF ALKYL XANTHOGEN FORMATES AND DIALKYL THIONOCARBAMATES AS COLLECTORS IN FROTH FLOTATION

[75] Inventor: Kim N. Unger, Tucson, Ariz.

[73] Assignee: Essex Industrial Chemicals, Inc., Clifton, N.J.

[21] Appl. No.: 835,982

[22] Filed: Mar. 4, 1986

[51] Int. Cl.[4] ....................... C09K 3/00; C07C 155/02; C07C 161/00

[52] U.S. Cl. ....................................... 252/61; 558/234; 558/244

[58] Field of Search .................... 252/61; 558/234, 244

[56] References Cited

U.S. PATENT DOCUMENTS

| | | | |
|---|---|---|---|
| 3,907,854 | 9/1975 | Bolth et al. | 252/61 |
| 4,454,051 | 6/1984 | Crozier | 252/61 |

*Primary Examiner*—Henry R. Jiles
*Assistant Examiner*—Robert C. Whittenbaugh
*Attorney, Agent, or Firm*—Harry M. Weiss & Associates

[57] ABSTRACT

The present invention provides a new collector for use in the froth flotation of metal values from their ores. The collector comprises a synergistic mixture of alkyl xanthogen alkyl formates and dialkyl thionocarbamates, and yields metal recoveries superior to that achieved with either collector alone. According to the present invention the novel collector for use in froth flotation comprises a mixture of alkyl xanthogen alkyl formates having the general formula:

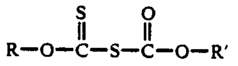

wherein R is a branched or straight chain alkyl substituent having 1 to 6 carbon atoms, and R′ is selected from the class consisting of ethyl and methyl; and dialkyl thionocarbamates having the general formula:

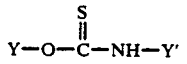

wherein Y is a branched or straight chain alkyl substituent having 1 to 6 carbon atoms, and Y′ is selected from the class consisting of ethyl and methyl.

8 Claims, No Drawings

MIXTURES OF ALKYL XANTHOGEN FORMATES AND DIALKYL THIONOCARBAMATES AS COLLECTORS IN FROTH FLOTATION

BACKGROUND OF THE INVENTION

Field of the Invention

This invention relates generally to ore dressing methods and to concentration of metal values in ores by flotation. More particularly, the invention provides a new and valuable method of rcovering metal values from ores, whereby froth flotation of a slurry of the ore is conducted in the presence of a synergistic collector consisting essentially of a mixture of certain alkyl xanthogen alkyl formate compounds with certain dialkyl thionocarbamate compounds.

Flotation is a widely used method of concentrating ores, and believed to be the most commonly used ore dressing process. It is based on the principle that when air bubbles are introduced into a ground ore pulp, particles of desired minerals will adhere to the air bubbles, be released from the ore and float to the surface. Other undesired minerals or gangue will not adhere to the air bubbles and will remain in the ore pulp. Certain chemicals facilitate the flotation process by conferring a water-repellency or hydrophobic property to the surface of the minerals. Chemicals which impart this hydrophobic or water-repellent property are generally called "promoters" or "collectors." Herein, they will be referred to as collectors.

Industrially, collectors for use in flotation are of great importance because even a very small improvement in collector efficiency can have a significant commercial benefit. With the growing current practice of tailings retreatment, the efficiency of the collector employed becomes increasingly significant. Additional concerns are toxicity and environmental conditions as well as ease of storage and handling.

SUMMARY OF THE INVENTION

Accordingly, an object of the present invention is to provide a collector for use in froth flotation which imparts improved metal recoveries.

Another object of the invention is to provide a flotation process wherein a collector is employed which imparts improved metal recovery at nominal cost, without substantial detriment to health and environment.

Yet another object of the invention is to provide a flotation method employing a synergistic mixture of alkyl xanthogen alkyl formates and dialkyl thionocarbamates as collectors.

A further object of this invention is to provide a froth flotation method yielding superior metallurgical recoveries than that obtained with either product alone.

A still further object of this invention is to provide a synergistic collector mixture capable of recovering a wide variety of metal values from their ores.

It is still a further object of this invention to provide a synergistic collector mixture capable of recovering metals from a wide variety of ores including chalcocite and chalcopyrite.

These and other objects hereinafter disclosed are provided by the invention wherein flotation of the ore is conducted in the presence of a collector comprising a mixture of (I) alkyl xanthogen alkyl formate compound of the formula:

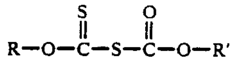

Wherein, R is a branched or straigh chain alkyl group consisting of 1 to 6 carbon atoms, and R' is selected from the class consisting of methyl and ethyl; and (II) dialkyl thionocarbamate compound of the formula:

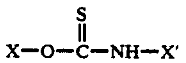

Wherein, X is a branched or straight chain alkyl group consisting of 1 to 6 carbon atoms, and X' is selected from the class consisting of methyl and ethyl.

Presently useful alkyl xanthogen alkyl formate compounds include:

isobutyl xanthogen ethyl formate
ethyl xanthogen ethyl formate
diethyl xanthogen formate
N-butyl xanthogen ethyl formate Presently useful dialkyl thionocarbamate compounds include:

N-methyl O-isobutyl thionocarbamate
N-ethyl O-methyl thionocarbamate

Alkyl xanthogen alkyl formates are particularly useful as flotation collectors in that they possess certain advantageous properties. These compounds are water insoluble oils and, thus, are not prone to depletion through absorption by slimes present in highly oxidized ore bodies. Where slime interference is present, high dosages of water soluble collectors, such as xanthates and dithophosphates, are generally required. However, since the alkyl xanthogen alkyl formates are not subject to surface absorption by slimes, improved recovery is observed at lower collector dosages. The alkyl xanthogen alkyl formates exhibit a high affinity for exceptionally fine mineral particles which are not readily collected by the xanthates and dithiophosphates. Moreover, like the xanthates, the alkyl xanthogen alkyl formates are highly selective against iron sulfide. Thus, they will satisfactorily collect copper, lead, zinc, molybdenum sulfide as well as the precious metals, while collecting lesser amounts of iron sulfide.

Like the alkyl xanthogen alkyl formates, the dialkyl thionocarbamates also possess certain characteristics which render them useful as flotation collectors. The dialkyl thionocarbamates are water insoluble oils, and are characterized by similar resistance to slime absorption. The principle difference in collector activity between the alkyl xanthogen alkyl formates and the dialkyl thionocarbamates is in the type of material for which each product has its highest affinity. The dialkyl thionocarbamates are particularly useful in the flotation of ores in which chalcocite is the predominate copper mineral; whereas the alkyl xanthogen alkyl formates are more commonly employed in the flotation of chalcopyrite.

The present invention demonstrates that mixtures of the dialkyl thionocarbamates and the alkyl xanthogen alkyl formates produce metallurgical yields superior to those obtained with either collector alone. This mixture produces a faster mineral load, better mineral flocculation and a beneficial froth structure. Improved recoveries are obtained not only on mixed chalcopyrite/chaltrocite ores but also on ores of a singular mineral type. Thus, the mixture of these two collectors demonstrates a synergistic potentiation of the activity of either collector alone. This synergistic mixture provides an improved flotation condition in general and is effective on all mineral types amenable to an ionic collector.

The invention is further illustrated, by, but not limited to, the following examples:

EXAMPLE I

A. 700 g or 10 mesh Phelps Dodge Copper Ore (Morenci, 0.55% Cu) was ground in a ball mill to 25.0%+65 mesh. 7.0 mg of a mixture consisting of 40% N-butyl O-ethyl thionocarbamate and 60% isobutyl xanthogen ethyl formate was added with 30 mg "Ore Prep F521" frother manufactured by Ore Prep. Flotation of the resulting mixture was for four minutes in a 2.0 L Wemco flotation machine at 1000 RPM. Concentrate copper recovery was 54.3%.

B. The same procedures were followed as in Part A except that 7.0 mg of isobutyl xanthogen ethyl formate was used as a collector. Concentrate copper recovery was 53.3%.

C. The same procedures were followed as in Example A above except that 7.0 mg of N-butyl O-ethyl thionocarbamate was used as a collector. Concentrate copper recovery was 52.5%.

EXAMPLE II

A. 800 g of 10 mesh Asarco Copper Ore (Mission, 2.63% Cu) was ground in a ball mill to 25.6%+100 mesh, 10 mg of a collector mixture consisting of isobutyl ethyl formate, ethyl xanthogen ethyl formate and N-isopropyl O-ethyl thionocarbamate and N-isobutyl O-methyl thionocarbamate was added with 45 mg of a frother consisting of methyl isobutyl carbinol (MIBC) and pine oil. The collector mixture consisted of 20% of the thionocarbamate blend and 80% of the alkyl xanthogen alkyl flotation blend. Flotation was for four minutes in a 2.0 L Wemco flotation machine at 1000 RPM. Concentrate copper recovery was 74.3%.

B. The same procedures as in Example A were followed except that 10 mg of the alkyl xanthogen alkyl formate blend was used. Concentrate copper recovery was 73.5%.

C. The same procedures were followed as in Example A above except that the 10 mg of total collector consisted of the dialkyl thionocarbamate blend. Concentrate copper recovery was 72.3%.

EXAMPLE III

A. 700 g of 10 mesh Anamax Copper Ore (Twin Buttes, 0.898% Cu) was ground in a ball mill to 6.5%+100 mesh. 10 mg of a collector mix consisting of 80% ethyl xanthogen ethyl formate and 20% N-isopropyl O-ethyl thionocarbamate and 25 mg of MIBC frother was added. Flotation was conducted for four minutes in a 2.0 L Wemco flotation machine at 1000 RPM. Concentrate copper recovery was 91.0%.

B. The same procedures as in Example A above were followed except that 10 mg of ethyl xanthogen ethyl formate were added as the collector. Concentrate copper recovery was 90.4%.

C. The same procedures as in Example A above were followed except that 10 mg of N-isopropyl O-ethyl thionocarbamate was added as the collector. Concentrate copper recovery was 89.0%.

D. The same procedures as in Example A above were followed except that 10 mg of a collector mix consisting of 80% ethyl xanthogen ethyl formate and 20% N-isopropyl O-ethyl thionocarbamate and n-isobutyl n-methyl thionocarbamate was added as the collector. Concentrate copper recovery was 90.8%.

E. The same procedures were followed as in Example A above except that 10 mg of ethyl xanthogen ethyl formate was added. Concentrate copper recovery was 90.4%.

F. The same procedures were followed as in Example A above except that 10 mg of N-isopropyl O-ethyl thionocarbamate and N-isobutyl O-methyl thionocarbamate was added. Concentrate copper recovery was 89.4%.

EXAMPLE IV

A. 700 g of 10 mesh Anamax Copper Ore (Twin Buttes, 1.36 Cu) was ground in a ball mill to 11.0%+100 mesh. 10 mg of a collector mixture consisting of 80% N-butyl xanthogen ethyl formate and ethyl xanthogen ethyl formate and n-isobutyl o-ethyl thionocarbamate and 15 mg of MIBC was added. Concentrate Copper recovery was 89.6%.

B. The same procedures as in Example A above were followed except that the 10 mg of collector consisted of a blend of N-butyl xanthogen ethyl formate. Concentrate Copper recovery was 71.8%.

EXAMPLE V

A. 700 g of 10 mesh Anamax (Twin Buttes, 1.51% Cu) ore was ground in a ball mill to 7.1%+100 mesh. 10 mg of collector mixture consisting of 80% ethyl xanthogen ethyl formate and 20% N-isopropyl O-ethyl thionocarbamate was added with 20 mg MIBC frother. Flotation was conducted for four minutes in a 2.0 L Wemco flotation machine at 1000 RPM. Concentrate copper recovery was 92.8%.

B. The same procedures were followed as in Example A above except that the 10 mg collector consisted of ethyl xanthogen ethyl formate. Concentrate copper recovery was 87.9%.

As may be readily observed from the herein described examples, the synergistic mixture of alkyl xanthogen alkyl formate collectors and dialkyl thionocarbamate collectors demonstrate significantly improved metal recoveries over that obtained with the individual collectors alone.

The herein described flotation procedures are given by way of illustration only. It will be understood to those skilled in the art that different flotation reagents may be used without departing from the spirit and scope of the present invention. Any ore dressing flotation technique may be used so long as the presently described synergistic mixture of alkyl xanthogen alkyl formate collectors and dialkyl thionocarbamate collectors are employed in the froth flotation.

What is claimed is:

1. A collector for use in froth flotation comprising a mixture of alkyl xanthogen alkyl formates having the general formula:

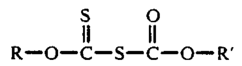

in a concentration in the range of about 60 to 80% by weight, wherein R is a branched or straight chain alkyl substituent having 1 to 6 carbon atoms and R' is an alkyl substituent selected from the class consisting of methyl and ethyl; and dialkyl thionocarbamate having the general formula:

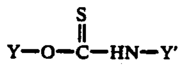

in a concentration in the range of about 20 to 40% by weight, wherein Y is a branched or straight chain alkyl substituent having 1 to 6 carbon atoms and Y' is an alkyl substituent selected from the class consisting of methyl and ethyl.

2. The collector of claim 1 further limited in that the alkyl xanthogen alkyl formate compound is isobutyl xanthogen ethyl formate.

3. The collector of claim 1 further limited in that the alkyl xanthogen alkyl formate is ethyl xanthogen ethyl formate.

4. The collector of claim 1 further limited in that the alkyl xanthogen alkyl formate is n-butyl xanthogen ethyl formate.

5. The collector of claim 1 further limited in that the dialkyl thionocarbamate collector is N-methyl O-isobutyl thionocarbamate.

6. The collector of claim 1 further limited in that the dialkyl thionocarbamate collector is N-ethyl O-methyl thionocarbamate.

7. The collector of claim 1 further limited in that said alkyl xanthogen alkyl formates comprise a blend of isobutyl xanthogen ethyl formate and ethyl xanthogen ethyl formate.

8. The collector of claim 1 further limited in that said dialkyl thionocarbamates comprise a blend of N-isopropyl O-ethyl thionocarbamate and N-isobutyl O-methyl thionocarbamate.

* * * * *